United States Patent [19]

LaForge et al.

[11] Patent Number: 4,488,099

[45] Date of Patent: Dec. 11, 1984

[54] REAL TIME SERVO CONTROL APPARATUS AND METHOD

[75] Inventors: David H. LaForge; Peer M. Portner, both of Kensington, Calif.

[73] Assignee: Novacor Medical Corporation, Oakland, Calif.

[21] Appl. No.: 446,452

[22] Filed: Dec. 3, 1982

[51] Int. Cl.³ .............................................. H02P 5/40
[52] U.S. Cl. .................................... 318/561; 318/615; 318/636; 3/1.7; 335/227; 128/1 D; 417/410
[58] Field of Search ............... 318/687, 615, 616, 617, 318/636, 561; 3/1.7; 335/227, 259, 267, 275; 128/1 D, DIG. 3; 417/410, 412

[56] References Cited

U.S. PATENT DOCUMENTS

| | | | |
|---|---|---|---|
| 984,748 | 2/1911 | Coleman | 335/259 X |
| 1,005,855 | 10/1911 | Lindquist | 335/229 |
| 1,893,776 | 1/1933 | Hull . | |
| 2,816,514 | 12/1957 | Freese . | |
| 3,071,714 | 1/1963 | Hadekel | 335/227 |
| 3,263,105 | 7/1966 | Heyek . | |
| 3,308,361 | 3/1967 | Nakai et al. . | |
| 3,633,217 | 1/1972 | Lance . | |
| 3,699,989 | 10/1972 | O'Connor et al. | 318/615 |
| 3,963,380 | 6/1976 | Thomas, Jr. et al. . | |
| 4,167,046 | 9/1979 | Portner et al. . | |
| 4,311,945 | 1/1982 | Aoyama | 318/615 X |
| 4,352,048 | 9/1982 | Schulze | 318/687 |
| 4,381,478 | 4/1983 | Saijo et al. | 318/687 |
| 4,384,829 | 5/1983 | Conley et al. . | |

OTHER PUBLICATIONS

Bindels, J., et al., *Trans. Amer. Soc. Artif. Int. Organs*, 7:369, 1961.

Bindels, John, *Trans. Amer. Soc. Artif. Int. Organs*, 8:140, 1962.

Freebairn, D., et al., *Trans. Amer. Soc. Artif. Int. Organs*, 10:166, 1964.

Fuller, J. W., et al., *Trans. Amer. Soc. Artif. Int. Organs*, 14:352, 1968.

Fuller, J. W., et al., *IEEE Trans. Biomed. Eng.* 16:184, 1969.

Portner, Peer M. et al., *7th Intersoc. Energy Conv. Eng. Conf. Proc.*, p. 784, (1972).

Jassawalla, J. S., et al., 10th Intersoc. Energy Conv. Eng. Conf., p. 1466, (1975).

Jassawalla, J. S., et al., Proc. 29th Ann. Conf. Eng. Med. Biol., p. 243, (1976).

Portner, P. M., et al., *Trans. Amer. Soc. Artif. Int. Organs*, 24:98 (1978).

Portner, Peer M., et al., *Artifical Organs*, vol. 2, No. 4, 402 (1978).

Portner, Peer M., et al., Proc. Annual Contractors Meeting, Devices and Technology Brancy, NHLBI, pp. 73-74 (1978).

Portner, Peer M., et al., Proc. Annual Contractors Meeting, Devices and Technology Branch, NHLBI, pp. 41-42 (1979).

*Primary Examiner*—B. Dobeck
*Attorney, Agent, or Firm*—Fitch, Even, Tabin & Flannery

[57] ABSTRACT

Real time servo control in a nonlinear, cyclical dynamic system adjusts the energy applied to a prime mover from a source of the energy as a linear function of an error between the measured load characteristics and modeled load characteristics. The modeled load characteristics are linearized as a function of the initial conditions of the load at the beginning of each cycle.

11 Claims, 9 Drawing Figures

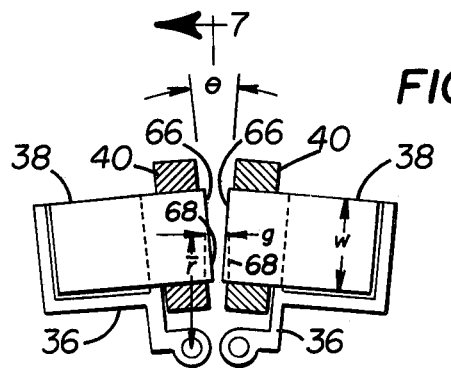
FIGURE 6
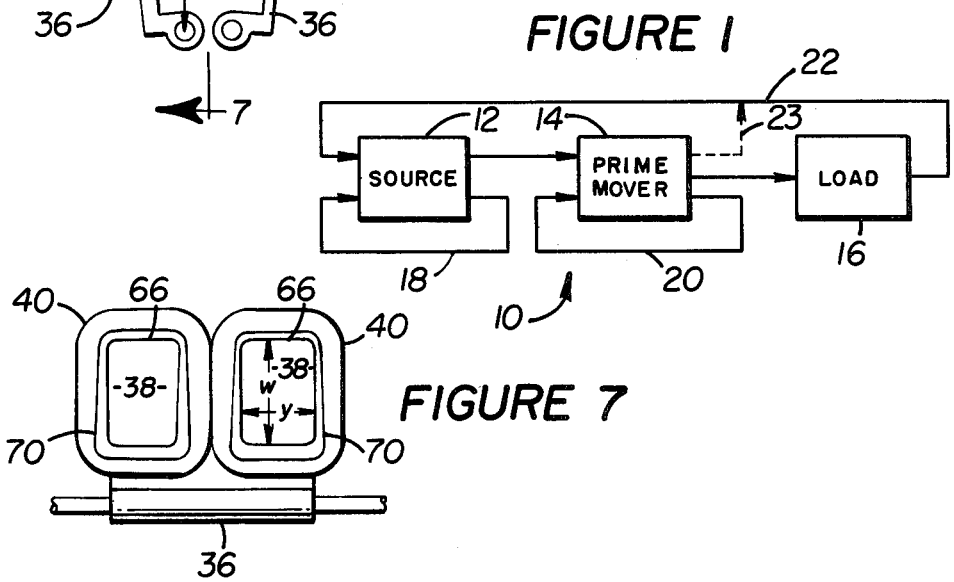
FIGURE 1
FIGURE 7
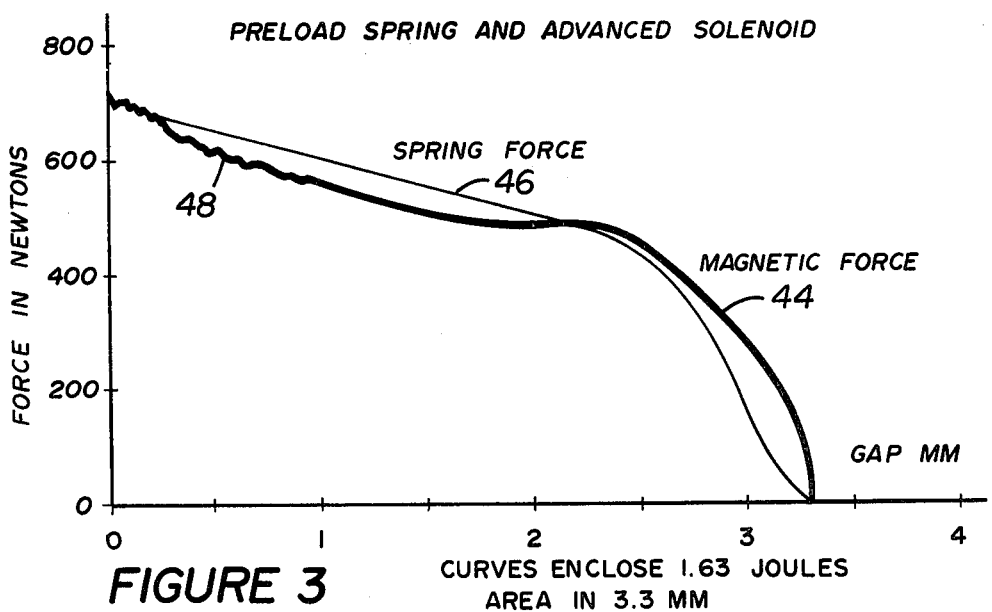
FIGURE 3

REAL TIME SERVO CONTROL APPARATUS AND METHOD

The present invention relates generally to a servo control apparatus and method and more particularly to a real time servo control apparatus and method for a dynamic electromechanical system.

BACKGROUND OF THE INVENTION

A typical dynamic electromechanical system has a source of electrical energy, a prime mover and a load. The prime mover is activated by the electrical energy applied to it to mechanically act on the load.

For example, two types of electromechanical systems include rotary DC motors or solenoids as the prime mover. In a rotary DC motor, the torque and angular velocity are linearly proportional to current and voltage, respectively. The system linearity simplifies servo control.

However, in the typical solenoid system, the source is unaware of the load. Variations in the load are not sensed by the source. The source is unable to alter the electrical energy applied to the prime mover in response to the variations in the load.

In order to perform real time servo control so that the source is aware of variations in the load, a model or algorithm must be formulated so that the feedback control to the source can be computed. However, such models and algorithms are generally non-linear and complex. Real time servo control is thus generally not possible. The amount of time required to compute the feedback control from non-linear and complex models and algorithms is much greater than the time in which variations in the load occur. Thus, real time servo control has been widely ignored in the art in solenoid systems, and the source has usually been designed to provide sufficient electrical energy for all expected load conditions. This practice usually has the result that the source is providing excess energy during most load conditions.

An example of such an electromechanical system is a solenoid activated cardiac assist pump of the type disclosed in U.S. patent application Ser. No. 211,210, filed Nov. 28, 1980. The pump disclosed therein has a solenoid, a pump bladder, and a pair of springs operatively coupled between the solenoid and bladder. The solenoid has a pair of C-shaped cores being disposed in a facing relationship with each other and normally biased apart from each other. Upon application of a current to the solenoid, such as by capacitive discharge, the cores are accelerated towards each other. The closing of the solenoid generates sufficient force in the springs to compress the bladder.

Since the springs are also used to bias the solenoid, the initial current must be sufficient to overcome the biasing spring force. Since the initial gap between the solenoid cores is unknown, and thus the amount of bias spring force is unknown, excessive current is applied to overcome such force. However, the successive current also results in excessive and undesirable impact energies when the solenoid cores strike against each other upon closure. In this device, the spring force profile and magnetic force profile were ideally matched in attempt to provide sufficient initial current to close the solenoid, and to balance the total spring and magnetic force to eliminate the impact energies. Because of the unknown initial gap, this approach also resulted in "misfires" when the gap was larger than predicted whereby the solenoid failed to close, or in excessive impact energies when the gap was smaller than predicted. Furthermore, when the solenoid reached closure, a snare pulse applied to the solenoid may have been required to assure latching.

SUMMARY OF THE INVENTION

It is therefore an important object of the present invention to overcome one or more of the disadvantages and limitations enumerated hereinabove.

It is another object of the present invention to provide a servo control apparatus and method for an entire dynamic electromechanical system.

It is yet another object of the present invention to provide a servo control apparatus and method which minimizes excessive impact energies in a solenoid.

It is still another object of the present invention in which the solenoid is linearly servo controlled in real time.

It is yet another object of the present invention to provide a servo control apparatus and method which linearizes the electromechanical system.

It is yet another object of the present invention to provide a servo control apparatus and method which does not require a snare pulse to close the solenoid after misfire or excessive impact.

According to the present invention, the non-linear system is characterized as a linear system, the linearities being dependent upon the systems initial conditions. The system may be represented by a set of non-linear equations. Parameters within the equations are dependent upon and are set by the initial conditions. By representing the system non-linearities within the parameters, the non-linear equations become a family of linear equations. Once the system has been so linearized, conventional servo control and/or feedback systems may be applied across the entire system.

Other objects, advantages adn features of the present invention from the following specification when read in conjunction with the accompanyings drawings and the appended claims.

BRIEF DESCRIPTION OF THE DRAWINGS

FIG. 1 shows a dynamic system illustrating feedback principles of the present invention;

FIG. 3 is an exemplary representation of magnetic force and spring force useful in practicing the method of the present invention;

FIG. 6 is a detail of a portion of the cardiac assist system shown in FIG. 2a–c; and FIG. 7 is a view taken along line 7—7 of FIG. 5.

DETAILED DESCRIPTION OF THE DRAWINGS

Figure 2A:
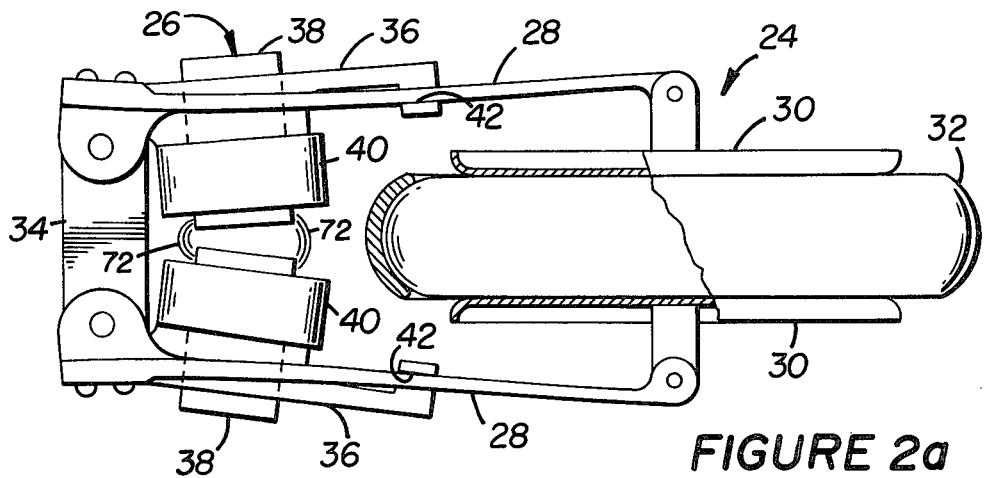
FIGS. 2a, 2b and 2c illustrate an exemplary cardiac assist system useful in practicing the method of the present invention.

FIG. 1 shows a dynamic system 10 having a source 12, a prime mover 14 and a load 16. Source 12 provides energy of a first type to prime mover 14. Such energy is transformed into energy of a second type by prime mover 14 to supply power to load 16. The transfer of energy through dynamic system 10 occurs in cycles, each cycle being independent and different from each other. Each independent cycle has different initial conditions. Each of source 12 and prime mover 14 may have feedback paths 18 and 20, respectively, which provide known functions. As a feature of the present invention, dynamic system 10 has a feedback path 22 from load 16 to source 12, or alternatively has a feedback path 23 from primer mover 14 to source 12, each feedback path 22 and 23 being for providing linear servo control.

Linear servo control along feedback path 22 or 23 is accomplished by determining the initial conditions of each cycle in dynamic system 10 and analyzing the transfer of energy to recognize when such energy transfer may be represented linearly as a function of such initial conditions. Thus, the flow of energy through dynamic system 10 may be represented by a family of linear equations. When such linearaties are established, conventional linear feedback techniques may be utilized for servo control.

Figure 2B:
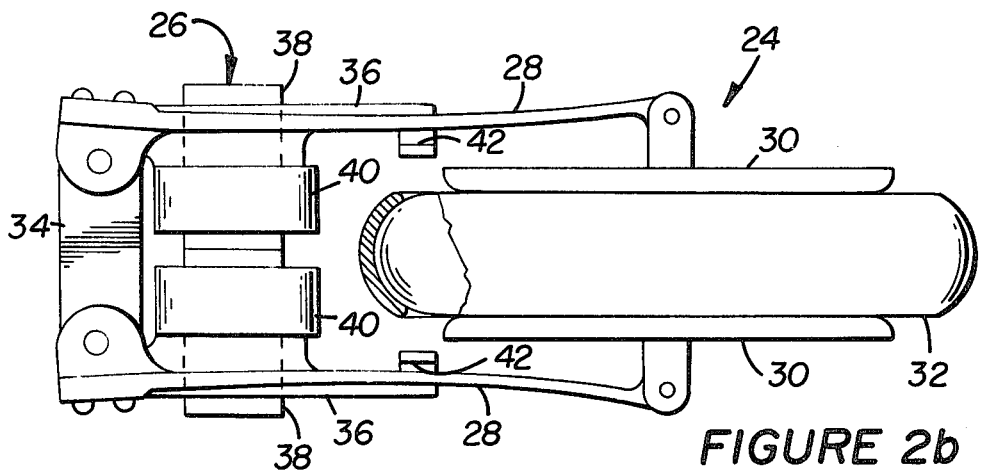
Figure 2C:
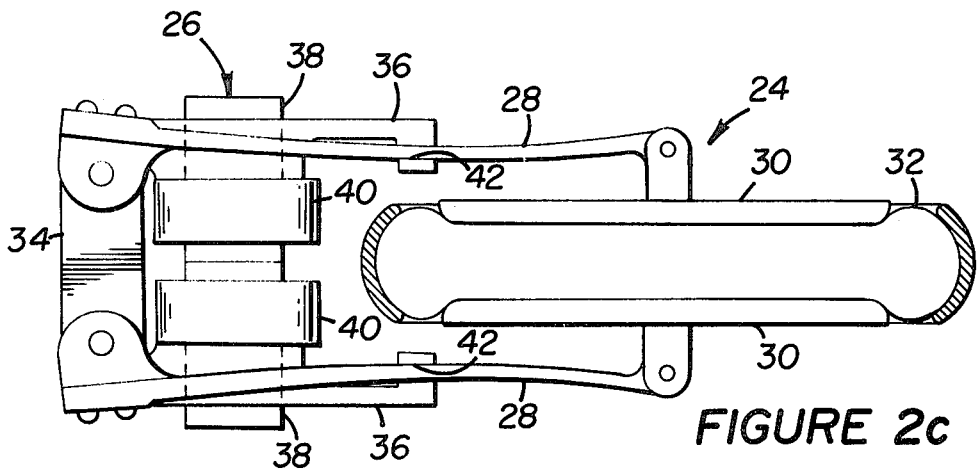

With reference to FIGS. 2a–c, the hereinabove described method of the present invention may be more particularly described in conjunction with an exemplary dynamic system illustrated as a cardiac assist system 24, the description of which is exemplary and not intended as a limitation upon the apparatus and method of the present invention.

Cardiac assist system 24 includes a source of electrical energy (not shown), a solenoid 26, a pair of beam springs 28, a pair of pusher plates 30, a pump sac 32, a frame 34 and a pair of solenoid supports 36. The complete description, function and interdependence of the elements shown in reference to cardiac assist system 24 has been fully described in U.S. patent application Ser. No. 211,210 filed Nov. 28, 1980, assigned to a predecessor of the assignee of the present invention, the relevant parts of which are incorporated herein by reference. However, cardiac assist system 24 will be described in enough detail to enable one skilled in the art to practice the method and apparatus of the present invention.

Solenoid 26 includes a pair of cores 38 and a pair of coils 40 disposed about a different one of each core 38. Each core 38 is supported by and fixed to a respective one of solenoid supports 36. Each solenoid support 36 is rotatably mounted to frame 34 so that solenoid cores 38 are in a facing relationship. Each beam spring 28 has one end fixed to a respective one of solenoid supports 36 and another end rotatably mounted to a respective one of pusher plates 30. Pump sac 32 is disposed in between pusher plates 30. Each solenoid support has a stop 42 at its distal end.

Cardiac assist system 24, as described, is one example of dynamic system 10 illustrated in FIG. 1. The source of electrical energy referred to but not shown in FIGS. 2a–c is generally represented by source 12 (FIG. 1). Solenoid 26 is one specific example of prime mover 14 (FIG. 1). Beam springs 28, pusher plates 30 and pump sac 32 represent one specific example of load 16 (FIG. 1).

The initial conditions to be determined in practicing the method of the present invention in conjunction with exemplary cardiac assist system 24 are best illustrated in FIG. 2a, wherein cores 38 of solenoid 26 are separated by an initial gap, $g(t=0)=g_i$, beam springs 28 are relaxed (except for a small preload between stop 42 and the end mounted to solenoid support 26), and pump sac 32 is filled.

FIG. 2b illustrates that solenoid 26 has been energized and magnetically latched in a closed position, and stops 42 are displaced from beam springs 28. Beam springs 28 exert a spring force on solenoid 26 in opposition to the magnetic latching force. Of course, each such spring force is also being exerted on pusher plates 30 for pumping liquid from the still filled pump sac 32.

FIG. 2c illustrates that the spring force exerted on pusher plates 30 has caused pump sac 32 to be compressed, thereby pumping liquid therefrom. In FIG. 2c, beam springs 28 are again relaxed and in contact with stops 42. Current may be removed from solenoid 26 and the next cardiac systole will fill pump sac 32, whereby cardiac assist system 24 returns to the initial state shown in FIG. 2a.

The volume of liquid returned to pump sac 32 during each cardiac systole is not constant. Thus the opening of pusher plates 30 in solenoid 26 varies during each cycle and is inherently non-linear. The gap of solenoid 26 at the end of filling of pump sac 26, which is of course the initial gap, $g_i$, as described in reference to FIG. 2a, inherits this non-linearity and has a different value at the beginning of each cycle. Another non-linearity is inherently in that the spring force acting in opposition to the magnetic force during the closing of solenoid 26 (the transition between FIG. 2a and FIG. 2b) is also dependent upon the initial gap, $g_i$.

FIG. 3 illustrates an exemplary diagram of the component forces acting on solenoid 26 during the transition between the positions of cardiac assist system 24 illustrated in FIGS. 2a and 2b. The component forces are illustrated as a magnetic force curve 44, which is the closing force acting on solenoid 26, and a spring force curve 46 acting in opposition to the closing of solenoid 26. The spring force illustrated at 46 is, in one embodiment, non-linear and has a profile selected to closely follow the magnetic force illustrated at 44 to minimize peak kinetic energies. The minimization of peak kinetic energies slow the closure of solenoid 26 to facilitate real time servo control. The servo control method of the present invention results in adjusting the magnetic force so that the area under each curve 44 and 46 is substantially equal whereby the total force acting on solenoid 26 is substantially zero. When the total force is zero, solenoid 26 achieves zero gap closing at zero velocity and zero acceleration. A region 48 of magnetic force curve 44 best illustrates the servo controlled variations in the magnetic force.

Figure 4:
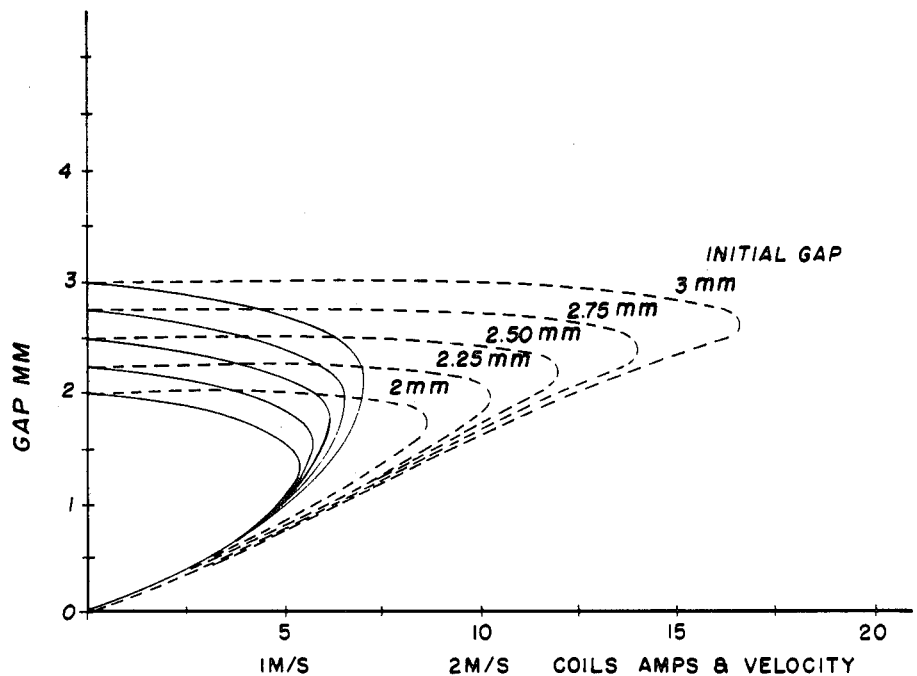
FIG. 4 is an exemplary representation of system linearities dependent on initial parameters useful in practicing the method of the present invention.

FIG. 4 illustrates various representations of current (dashed lines) through coils 40 and the velocity (solid lines) of solenoid 26 which the rate of closure of gap, g. The current and velocity are shown with the initial gap, $g_i$, as a parameter. It is noted that the current peak occurs approximately at two thirds of the initial gap. The current locus, after peak current occurs, is rectilinear and the gap at which peak current occurs linearly depends on the initial gap. Of course, FIG. 4 is valid when the current is developed by capacitive discharge. Thus after peak current has occurred, cardiac assist system 24 may be represented as a linear model.

One feature in representing cardiac assist system 24 as a linear model is that, after capacitive discharge, a "coast" voltage, $v_s$, may be applied to solenoid 26 which is equal to the mean resistive voltage drop of coil 40. The coast voltage, $v_s$, is dependent only on initial gap, $g_i$, in the linear model. The servo control method of the present invention controls the "coast" voltage, $v_s$, as a function of the velocity of solenoid 26, the velocity being dependent on the initial conditions of the load (initial gap) as illustrated in FIG. 3. Since the velocity which depends on load can be represented as a family of linear equations dependent only on initial gap, $g_i$, servo control is possible across cardiac assist system 24, similarly as hereinabove generally described with reference to dynamic system 10 in FIG. 1.

More particularly, after peak current, the current, i, may be written as a function of gap, g, or $$i = \lambda g \qquad (1)$$

where $\lambda$ is the slope which is dependent on initial gap, $g_i$. It is known that the inductance, L, of coils 40 is given by $$L = k/g \qquad (2)$$

where k is the magnetic core constant of cores 38. The coast voltage, $v_s$, in the linear model may be given by $$v_s = ir + d(Li)/dt \qquad (3)$$

where ir represents the resistive voltage drop of coil 40. In the linear model, the term $d(Li)/dt$ of Eq. (3) can be shown to be equal to zero by substitution of the values of L and i given in Eq. (2) and Eq. (1), respectively, and thus, Eq. (3) reduces to $$v_s = ir. \qquad (4)$$

Substitution of Eq. (1) into Eq. (4) shows that the coast voltage, $v_s$, is then linearly dependent on initial gap, $g_i$, by $$v_s = \lambda g r \qquad (5)$$

since $\lambda$ is dependent only on initial gap, $g_i$.

Where the actual velocity of solenoid 26 deviates from the ideal velocity shown in FIG. 4, a magnetic force offset, $\Delta f$, can be described. Since the current versus gap relationship is still substantially linear, although the actual current deviates from the ideal current by current offset, $\Delta i$, the magnetic force offset, $\Delta f$, is also linear and can thus be compensated for by a correction voltage, $v_e$, superimposed on the coast voltage, $v_s$.

It is known that magnetic force, $f_{mag}$, may be given by $$f_{mag} = -ki^2/2g^2. \qquad (6)$$

Where the actual current deviates from the ideal current by the current offset, $\Delta i$, the magnetic force offset may be derived from Eq. (6) and shown to be equal to $$\Delta f = -k\lambda \Delta i/g. \qquad (7)$$

Eliminating the gap dependency term in a magnetic force offset, $\Delta f$, by substituting Eq. (2) into Eq. (7), $$\Delta f = -\lambda v_e \Delta t. \qquad (8)$$

In a matched closure condition, i.e. when terminal velocity equals zero and the actual current equals the ideal current, the magnetic force given in Eq. (6), by substituting Eq. (1) therein, is independent of gap. Therefore the characteristic motion of solenoid 26 is forced harmonic, governed by its inertial mass and spring force (FIG. 3).

From harmonic equation analysis, a family of glide paths may be determined from which feedback control equations may be developed. However, the exact glide path equations need not be used. Servo control is thus based on the establishment of a system linearity about known normal characteristics which permit error free superposition of succeeding corrective actions. Thus, a correction signal can be added without invalidating previously computed corrections. A harmonic character of the motion makes possible simultaneous nulling of the net force and of the velocity at zero gap since the acceleration, velocity and gap are at 90° phases.

Figure 5:
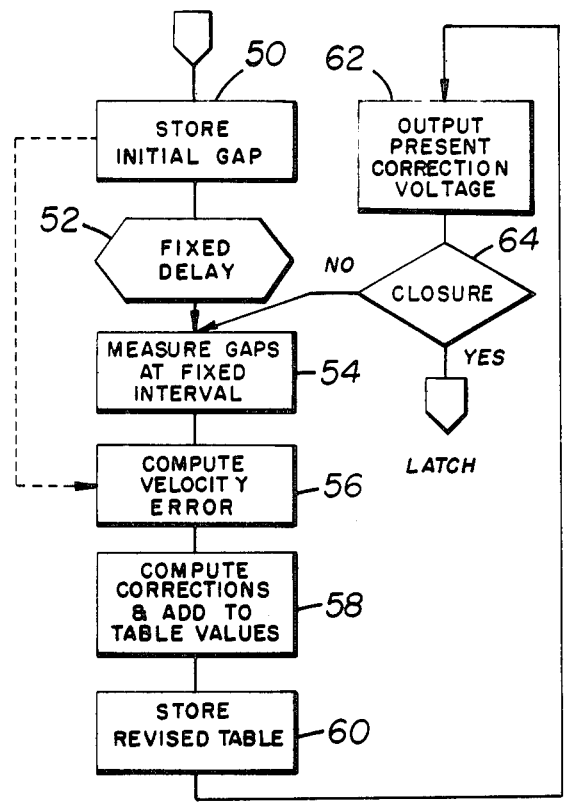
FIG. 5 is a flow chart illustrating one embodiment of a method according to the present invention.

Referring now to FIG. 5 there is shown a flow chart for a servo algorithm, in one embodiment of the present invention, which may incorporate the above described relationships and equations. The first step of the servo method is to measure and store the initial gap of solenoid 26, as indicated at 50. Indicated at 52, the method includes a fixed delay selected commensurately with the time interval between capacitive discharge and maximum velocity as shown in FIG. 3. After the velocity of solenoid 26 has reached its maximum, the instantaneous gap, g, may be measured at fixed time intervals as indicated at 54. From the instantaneous gap measured at the fixed time intervals, the velocity of solenoid 26 may also be computed. Indicated at 56, it is seen that the instantaneous rate of closure, i.e. the velocity of solenoid 26, is compared to the ideal model values which may be determined from FIG. 4. From this comparison the velocity error may be calculated as the difference between the instantaneous measured velocity and the ideal velocity given by the model.

Indicated at 58, the corrections from the velocity error are computed and added to the ideal model. If no velocity error was computed at 56, the computing method at 58 includes reading the current through coils 40, and computing a force imbalance, $f_2$, that exists during closure. This force imbalance, $f_2$, is added algebraically to the magnetic force offset, $\Delta f_1$, such that $$\Delta f + f = 0 \qquad (9).$$

The correction voltage, $V_e$, may then be determined as hereinabove described and superimposed upon the coast voltage, $V_s$.

If at 56 a velocity error is computed, such error is compared with the last such velocity error computed in a prior reiteration of the method. If the velocity error is not worse than the prior, the method includes estimating the time to close solenoid 26, and computing the corrective force which is given by the well known equation $f = m\Delta u/t$. The method then includes the steps as if no velocity error was present.

If the velocity error is worse than the prior computed velocity error, a determination is made whether such error is higher or lower than the prior error.

Indicated at 60, it is indicated that the corrections hereinabove described are stored and added to the model.

Indicated at 62, the necessary corrections are used to determine the error correction voltage, $V_e$, to be superimposed upon the coast voltage, $V_s$, or if a dump or a boost voltage, is to be superimposed. The dump or boost voltage is applied whenever the velocity error is worse than a prior velocity error, or if a force error exists when there is no velocity error.

At 64, it is indicated that a determination is made is solenoid 26 has closed, i.e. gap g=0. If there is not closure, the steps of the hereinabve described method, commencing at step 34, are repeated. If there is a closure, the method further includes computing of force imbalance between the magnetic latching force and the spring force at closure. If there is a sufficient latching force, the method terminates. If there is an insufficient latching force, i.e., spring force greater than magnetic force, a snare pulse is applied to solenoid 26 and more particularly to coils 40 to assure latching of the device.

Another feature of the present invention is described with reference to FIGS. 6 and 7. Each face of cores 38 define a pole 66 having a width w and an height y. Poles 66 are, of course, disposed in a facing relationship with each other which defines the gap, g. An angle $\theta$ is defined between the poles 66, the gap, g, being measured at the midpoint of poles 66, as best seen if FIG. 6.

A feature of the present invention is that at full gap, i.e. the gap, g, at a maximum, and when the magnetic field intensities between each pole 66 is operated slightly below saturation, a pole tip region 68 becomes saturated. As solenoid 26 closes, and the gap, g, decreases, saturated region 20 "travels" across pole 66 along its width w. The energy transfer of this design allows minimization of the pole area given by wy, but achieves the same energy transfer of an equivalent pole 70 operated at saturation. Qualitatively, because mganetic stored energy depends upon the square of the flux density, a nonuniform gap stores more energy for the same total flux then a uniform gap of the same volume. The design of solenoid 26 also takes advantage of the initial fringing fields indicated at 72 as best seen in FIG. 2a. The initial fringing field adds to the total magnetic force to give the magnetic force profiles shown in FIG. 4. With the fringing fields, the magnetic field is comparable to a homogenous field between each forcing equivalent pole 70. Since the solenoid is symmetrical about its w-y axis, the magnetic force curve 44 shown in FIG. 2 becomes linearized as an effect of fringing fields 72.

Various modifications of the invention in addition to those shown and described herein will become apparent to those skilled in the art from the foregoing description and accompanying drawings. Such modifications are intended to fall within the spirit and scope of the appended claims.

What is claimed is:

1. In a dynamic system having a source of energy of a first type, a prime mover for converting said energy of said first type to energy of a second type, and a load, said prime mover applying said energy of said second type to said load, the converting of said energy occurring in cycles, each cycle being independent from each other, each independent cycle having different initial conditions of said load, a method for linear servo control of said source in response to variations in said load comprising:

formulating a model of said dynamic system to determine an operating point about which said dynamic system exhibits linear behavior, said operating point being a function of said initial conditions of said load during each said cycle;

modeling the energy requirements of said load to maintain said linear behavior and further modeling the amount of energy to be applied by said source as a function of said energy requirements of said load;

modeling the energy requirements of said prime mover to maintain said linear behavior;

determining the initial conditions of said load for each said cycle;

computing the difference between the actual energy requirements of said load during each said cycle from said modeled energy requirement; and adjusting the energy developed by said source by an incremental amount which is linearly proportional to the difference between said energy requirements and said modeled energy requirements.

2. In a solenoid having a pair of poles and a facing relationship to each other and normally biased apart from each other defining a gap therebetween, a method for optimizing energy transfer of said solenoid comprising;

rotatably mounting each of said poles whereby said gap is nonuniform when said poles are biased apart from each other; and energizing said solenoid with a current selected to limit a saturation region of said poles initially to a first pole tip region thereof, said saturation region transversing said poles during closure of said gap, said saturation region increasing magnetic stored energy for enhancing effective cross sectional area of said poles defining an equivalent nonsaturating virtual pole of greater cross sectional area than each of said poles.

3. A method in accordance with claim 2 wherein said saturation region at said first pole tip region develops a fringing field outside of the cross sectional area of said poles, said fringing field effectively linearizing the magnetic force developed between said poles.

4. A method in accordance with claim 2 wherein said nonuniform gap further increases magnetic stored energy further enhancing effective cross sectional area of said poles.

5. In a dynamic system having a source of electrical energy, a solenoid, and a load, said energy being applied to said solenoid, said solenoid closing to transfer said energy to said load, said solenoid having a pair of poles in a facing relationship to each other in normally biased apart from each other defining a gap therebetween, a method for servo controlling said source in response to variations of said load, said method comprising the steps of:

a. measuring an initial width of said gap;

b. measuring an instantaneous width of said gap at selected time intervals after applying energy to said solenoid;

c. computing an instantaneous velocity of said solenoid from each instantaneous width and computing an error between each instantaneous velocity and a predetermined velocity;

d. adjusting said energy applied to said solenoid by an incremental amount, said incremental amount being a linear function of said error.

6. A method in accordance with claim 5 further comprising the step of repeating steps b-d until said solenoid is closed.

7. A method in accordance with claim 5 wherein said computing step further includes repeatedly computing said error and comparing each computed error with the immediately preceeding computed error, and superimposing a predetermined incremental amount of energy upon said energy applied to said solenoid whenever said computed error is greater in magnitude than the immediately preceeded computed error.

8. A method in accordance with claim 7 wherein said incremental amount of energy lessens the total energy applied to said solenoid at said velocity error indicate that said solenoid has a higher velocity than the predetermined velocity.

9. A method in accordance with claim 7 wherein said incremental amount of energy increases the total energy applied to said solenoid whenever said velocity error indicates said solenoid has a velocity less than said predetermined velocity.

10. A method in accordance with claim 5 which further includes computing a force imbalance between the magnetic latching force and a spring force acting in opposition to said magnetic force when said solenoid has closed.

11. A method in accordance with claim 10 wherein a snare pulse is applied to said solenoid whenever said force imbalance indicates said spring force is greater than said magnetic force.

* * * * *